United States Patent [19]

Terashima et al.

[11] Patent Number: 4,900,665
[45] Date of Patent: Feb. 13, 1990

[54] INTEGRAL MULTILAYER ANALYTICAL ELEMENT FOR USE IN THE MEASUREMENT OF ALKALINE PHOSPHATASE ACTIVITY

[75] Inventors: Kaoru Terashima; Shigeki Kageyama; Harumi Katsuyama, all of Saitama, Japan

[73] Assignee: Fuji Photo Film Co., Ltd., Kanagawa, Japan

[21] Appl. No.: 185,294

[22] Filed: Apr. 19, 1988

Related U.S. Application Data

[63] Continuation of Ser. No. 794,110, Nov. 1, 1985, abandoned.

[30] Foreign Application Priority Data

Nov. 2, 1984 [JP] Japan ............................... 59-230239

[51] Int. Cl.$^4$ ......................... C12Q 1/42; G01N 31/22
[52] U.S. Cl. ......................................... 435/21; 422/56; 422/57; 422/58; 435/805
[58] Field of Search ............... 422/56, 57, 58; 435/21, 435/805

[56] References Cited

U.S. PATENT DOCUMENTS

| 3,802,842 | 4/1974 | Lange et al. ..................... 422/57 X |
| 4,030,995 | 6/1977 | Starkweather ................. 435/814 X |
| 4,132,598 | 1/1979 | Modrovich ........................... 435/21 |
| 4,166,766 | 9/1979 | Metzenberg et al. .......... 435/815 X |
| 4,306,020 | 12/1981 | Meiattini ............................. 435/21 |
| 4,555,484 | 11/1985 | LaRossa et al. ................ 435/805 X |

OTHER PUBLICATIONS

Ellis, Chem. Abstracts, 84 (17):117450X
McComb, et al., Clinical Chemistry, (18/2), pp. 97–104.

*Primary Examiner*—Barry S. Richman
*Assistant Examiner*—Jill Johnston
*Attorney, Agent, or Firm*—Jules E. Goldberg

[57] ABSTRACT

An integral multilayer analytical element for use in the measurement of alkaline phosphatase activity, which comprises a porous spreading layer of woven fabric or knitted fabric containing an alkaline phosphatase-sensitive self-developing substrate, a buffer layer containing one or more compounds functioning as a phosphoric acid acceptor and a buffering agent and a support layer in a laminated form.

7 Claims, 1 Drawing Sheet

INTEGRAL MULTILAYER ANALYTICAL ELEMENT FOR USE IN THE MEASUREMENT OF ALKALINE PHOSPHATASE ACTIVITY

This is a continuation of application Ser. No. 794,110, filed Nov. 1, 1985 and now abandoned.

BACKGROUND OF THE INVENTION

1. Field of the Invention

The present invention relates to an integral multilayer analytical element for use in measuring alkaline phosphatase activity in a liquid sample, and more particularly to an integral multilayer analytical element for use in measuring alkaline phosphatase activity useful for the analysis of aqueous liquid samples, particularly for clinical test using body fluids as samples.

2. Description of Prior Arts

It is very important to measure alkaline phosphatase activity present in the human body fluid in clinical test. Accordingly, the measurement of alkaline phosphatase (hereinafter, sometimes, referred to as ALP) activity in the body fluid has been made in the diagnoses of hepatopathy including obstructive jaundice and bone diseases including osteoncus.

Since a method for measuring alkaline phosphatase activity had been proposed by H. D. Kay [see, J. Biol. Chem., 88 235 (1930)], various methods have been studied and proposed. Particularly, the measurement had been efficiently simplified by a method developed by E. J. King [see, Biochem. J., 33 1185, 1939], wherein an aryl phosphate or the aryl phosphate, especially a self-developing p-nitrophenyl phosphate is used as the substrate.

The above-mentioned measuring method have been further studied by researchers. As a result, it has been found that the optimum pH in the color forming reaction is about 10, that the presence of a certain alcohol is preferred, and that an inorganic ion, particularly magnesium ion, is preferably present as an activator. Thus, there has been established IFCC method [see, Clin. Chimica, Acta., (1983) 339F–367F] wherein disodium p-nitrophenyl phosphate is used as a substrate.

However, this method has disadvantages in that the solution of disodium p-nitrophenyl phosphate must be prepared just at the time of measurement and is unstable. The time during which the solution can be preserved at 20° to 26° C. is only for 8 hours at most. Further, disodium p-nitrophenol phosphate is unstable even at freezer temperatures as pointed out by Amador. E., et al. [see, J. Amer. Med. Ass., 184 953 (1963)]. Accordingly, the potency of the reagent must be assayed before measurement and great care must be taken of the preservation of the reagent during the period of time from the preparation through measurement.

The problem in the instability of disodium p-nitrophenyl phosphate has been greatly improved by the method described in Japanese Patent Publication No. 45(1970)34827 wherein an organic amine salt of p-nitrophenyl phosphate are used. Further, an amine salt of thymolphthalein monophosphate which has an absorption spectrum in the region of wavelengths longer than that of p-nitrophenyl phosphate has been synthesized by John M. Ellickson, et al. [see, Clinical Chemistry, Vol. 19, No. 6, 1973, page 664]. The preservation of the substrates per se have been thus greatly improved, and it becomes possible that the substrate can be easily incorporated in a reagent kit for the measurement of ALP.

A rapid measurement system with a simple operation in clinical test is highly desired by medical persons such as medical doctors. Hence, methods for measuring ALP using integral multilayer analytical elements which are easy to handle have been developed and the improvements of the elements are being made.

An example of such integral multilayer analytical element comprises a water-absorbing layer containing a color forming reagent and a hydrophilic polymer binder and a porous spreading layer provided on a transparent support as reported by B. Walter [see, Analytical Chemistry, (1983) 55 498A]. Further, a number of other analytical elements have been known.

However, in order to perform the analysis of ALP using a dry analytical method, the degree of the improvement in the preservation of substrates such as p-nitrophenyl phosphate, etc. is still unsatisfactory. Therefore, it is highly desired to develop an integral multilayer analytical element for use in measuring alkaline phosphatase activity, which is free from the problem of insufficient preservation, particularly insufficient preservation of substrate.

SUMMARY OF THE INVENTION

The inventor has made studies on the method for measuring alkaline phosphatase activity by the conventional dry method and the instrument (integral multilayer analytical element) used therefor and found that when an amino-alcohol serving as a phosphoric acid acceptor or a basic buffering agent buffering at a pH of about 10 to 11 and a substrate such as an aryl phosphate amine salt are contained in the same layer in the conventional analytical method, the buffering agent or the amino-alcohol is brought into contact with the substrate during the storage of the analytical element and as a result, the preservation of the substrate such as the aryl phosphate amine salt is greatly deteriorated, though the substrate in a crystalline form before contact is stable.

Since self-developing substrates for alkaline phosphatase are usually substituted phosphate esters containing electron attractive group, they are liable to undergo non-enzymatic hydrolysis. Particularly, the presence of a buffering agent buffering at a pH of about 10 to 11 which is the optimum pH for alkaline phosphatase, detection accelerates the decomposition, particularly the non-enzymatic hydrolysis of the aryl phosphate substrate.

The non-enzymatic hydrolysis of the substrate occurs not only during the storage of the analytical element, but also at the time of the preparation thereof. Therefore, the dye concentration of the analytical element before the analysis of a sample serving as blank at the time of measurement is higher than that after the analysis so that analytical accuracy is lowered even when the analytical element is used for the measurement immediately after the element is prepared.

It is an object of the present invention to provide an integral multilayer analytical element for use in the measurement of alkaline phosphatase activity, which is free from the above-described disadvantages associated with the conventional integral multilayer analytical elements in dry analytical methods.

It is another object of the invention to provide an integral multilayer analytical element which can be operated readily and rapidly and can be easily used for the measurement of alkaline phosphatase activity in liquid samples in clinical test by medical doctors and nurses who may be inexperienced in the test.

The present invention provides an integral multilayer analytical element for use in the measurement of alkaline phosphatase activity, which comprises a porous spreading layer of woven fabric or knitted fabric containing an alkaline phosphatase-sensitive self-developing substrate, a buffer layer containing one or more compounds functioning as a phosphoric acid acceptor and a buffering agent and a support layer in a laminated form.

The integral multilayer analytical element of the invention for use in the measurement of alkaline phosphatase activity has a structure such that the porous spreading layer of woven fabric or knitted fabric (hereinafter referred to as spreading layer) contains a self-developing substrate and the buffer layer contains a phosphoric acid acceptor, so that there is no possibility that the phosphoric acid acceptor and the buffering agent are brought into contact with the substrate at the time of the preparation of the analytical element and during storage.

Thus, the integral multilayer analytical element of the invention for use in the measurement of alkaline phosphatase activity has advantages in that there is greatly reduced a possibility that the substrate undergoes non-enzymatic hydrolysis and hence the preservation of the substrate is made remarkably stable so that the preparation of the analytical element becomes easier and the stability thereof is greatly improved.

As described above, the substrate does not undergo non-enzymatic hydrolysis even at the time of the preparation of the multilayer analytical element according to the invention, though the conventional analytical elements undergo non-enzymatic hydrolysis. Accordingly, the integral multilayer analytical element of the invention has an advantage in that the measurement can be made with high accuracy even immediately after the preparation thereof, as compared with the conventional elements for use in the measurement of ALP activity.

BRIEF DESCRIPTION OF THE DRAWING

The drawing shows an analytical element in accordance with the present invention.

DETAILED DESCRIPTION OF THE INVENTION

Figure 1:
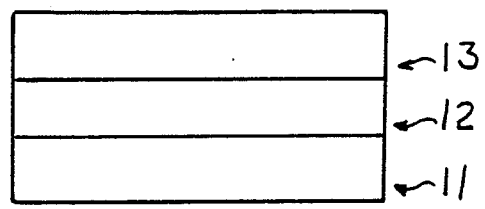

As shown in the drawing, the analytical element of the present invention comprises a support 11, a buffer layer 12, and an alkaline phosphatase-sensitive self-developing substrate containing a porous layer of a woven or knitted fabric 13, arranged in the sequence shown.

The preferred support employable in the integral multilayer analytical element for use in the measurement of ALP activity of the invention is a liquid-impermeable light-transmissive support. Examples of such support include transparent supports (films and sheets) made of a polymer such as polyethylene terephthalate, polycarbonate of bisphenol A, polystyrene and cellulose esters (e.g., cellulose diacetate, cellulose triacetate, cellulose acetate propionate etc.). The thickness of the support generally ranges from approx. 50 μm to approx. 1 mm, preferably from approx. 80 μm to approx. 300 μm.

There may be provided an undercoating layer on the support to enhance the adhesion between the support and a buffer layer or optionally added other intervening layer (e.g., absorbent layer). Instead of the undercoating layer, the surface of the support may be activated by physical or chemical process to enhance the adhesion.

There is provided a buffer layer on the support (optionally, intervened by other layers, such as the undercoating layer). The buffer layer of the invention is preferably a layer formed of a hydrophilic binder. The binder is preferably a hydrophilic polymer which may absorb water to swell.

The hydrophilic polymer preferably shows swelling ranging from approx. 150% to approx. 2000%, more preferably from approx. 250% to approx. 1500%. at 30° C. Examples of the hydrophilic polymer satisfying the above-described conditions include gelatin (e.g., acid-processed gelatin, deionized gelatin etc.), gelatin derivatives (e.g., phthalated gelatin, hydroxyacrylate grafted gelatin etc.), agarose, pullulan, pullulan derivatives, dextran, polyacrylamide, polyvinyl alcohol, and polyvinyl pyrrolidone.

The thickness of the buffer layer preferably ranges from approx. 1 μm to approx. 100 μm, more preferably from approx. 3 μm to approx. 30 μm. The buffer layer is preferably transparent.

The buffering agent to be incorporated in the buffer layer is chosen from those which buffer at a pH of about 10 to 11 (which is the optimum pH for alkaline phosphatase which is an analyte) and do not show an adverse effect, for example, do not interfere with reaction.

Examples of such buffering agents include the conventional agents such as carbonates, borates, phosphates and Good's buffering agents. These buffering agents can be chosen from those shown in the literature "Fundamental Experimental Method for Protein and Enzyme" by Takeichi Horio, et al. (Naneido, 1981, written in Japanese). Further, known compounds which are effective in measuring ALP activity, such as diethanolamine, 2-(ethylamino)ethanol, tris(hydroxymethyl)aminomethane, diethylamine, 2-(methylamino)ethanol and 2-(isopropylamino)ethanol can be used by basing on the disclosures of literatures such as Clinical Chemistry, Vol 18, No. 2, 1972, 97–104 by B. McComb, et al. Among them, some compounds serve as both a buffering agent and a phosphoric acid acceptor as described in more detail hereinafter.

In the integral multilayer analytical element of the invention, the phosphoric acid acceptor is incorporated in the buffer layer. The term "phosphoric acid acceptor" used herein refers to a compound containing a functional group (for example, hydroxyl group) whose reaction with phosphoric acid formed from the substrate by the action of alkaline phosphatase proceeds prior to a reaction (hydrolysis) between phosphoric acid and water. By using the phosphoric acid acceptor, the desired reaction is expedited, the enzymatic activity of the analyte is increased, and as a result, the detecting accuracy is improved.

The preferred phosphoric acid acceptor to be incorporated in the buffer layer is an amino-alcohol. Though there can be used amino-alcohols which are generally proved to be effective as the phosphoric acid acceptor, such as diethanolamine (pKa 8.7), 2-amino-2-methyl-1,3-propanediol (pKa 8.6) and tris(hydroxymethyl)aminomethane (pKa 7.8), amino-alcohols having a pKa value of 9.0 or above are preferably employed in the integral multilayer analytical element of the invention for use in the measurement of ALP activity. It has been found that the preservation of the substrate is greatly improved when an amino-alcohol having a pKa value of 9.0 or above is used in the integral multilayer analytical element of the invention.

The amino-alcohols having a pKa value of 9.0 or above are reported in the aforementioned literature by McComb, et al. The preferred examples of such amino-alcohol include 2-aminoethanol (pKa 9.2), 2-(ethylamino)ethanol (pKa 9.9), 2-(methylamino)ethanol (pKa 9.6), 2-(dimethyl-amino)ethanol (pKa 9.2), 2-(isopropylamino)-ethanol (pKa 9.9), 2-amino-2-methyl-1-propanol (pKa 9.3), 3-aminopropanol (pKa 9.4), DL-2-amino-1-propanol (pKa 9.4), hydroxy-proline (pKa 9.4) and N-methylglucamine.

When an amino-alcohol is used as a phosphoric acid acceptor in the buffer layer, the amino-alcohol functions as a buffering agent capable of giving the optimum pH for the enzymatic reaction as well, so that the buffer layer can be formed without independently incorporating a buffering agent.

There may be provided a light-blocking layer on the buffer layer. The buffer layer is a water-permeable layer in which light-blocking (or light-reflecting) fine particles are dispersed in small amount of a film-forming hydrophilic polymer binder. The light-blocking layer may function as light-reflecting layer or background layer as well as blocker to the color of an aqueous liquid spotted on the spreading layer, such as the red of hemoglobin in whole blood sample, when a detectable change (a color change or a color development etc.) in the buffer layer is measured from the side of the transparent support reflection photometry.

Examples of light-blocking and light-reflecting particle include titanium dioxide fine particles (rutile-type, anatase-type or brookite-type; mean size ranging from approx. 0.1 $\mu$m to approx. 1.2 $\mu$m), barium sulfate fine particles, aluminum fine particles and fine flakes thereof. Examples of light-blocking particle include carbon black, gas black and carbon microbeads. Most preferred are titanium dioxide fine particles and barium sulfate fine particles.

Examples of the film-forming hydrophilic polymer binder include a weakly hydrophilic polymer such as regenerated cellulose and cellulose acetate as well as the hydrophilic polymer employable in the buffer layer. Most preferred are gelatin, gelatin derivatives and polyacrylamide. Gelatin and gelatin derivatives may be used as a mixture with a known hardening agent (cross-linking agent).

The light-blocking layer can be prepared by using such manner that aqueous disperse liquid containing the light-blocking particle and the hydrophilic polymer is coated and then dried on the buffer layer. Instead of the light-blocking layer, the light-blocking particles may be incorporated in the spreading layer.

There may be provided an adhesive layer on the buffer layer or optionally added other layer (e.g., light-blocking layer) to enhance the adhesion of the spreading layer.

The adhesive layer is preferrably constituted by a hydrophilic polymer which can bond the spreading layer to other layer to make all of the layers integrated while the polymer is wetted or swelled with water. Examples of the hydrophilic polymer include the polymer employable in the buffer layer. Most preferred are gelatin, gelatin derivatives and polyacrylamide. The dry thickness of the adhesive layer generally ranges from approx. 0.5 $\mu$m to approx. 20 $\mu$m, preferably from approx. 1 $\mu$m to approx. 10 $\mu$m.

The adhesive layer may be provided on other layers as well as on the buffer layer. The adhesive layer can be prepared by using such manner that a solution of the hydrophilic polymer and optionally added other agent such as a surfactant is coated on the buffer layer or other layer.

A porous spreading layer of woven fabric or knitted fabric is provided on the layer. The porous spreading layer preferably has a metering effect (i.e., metering the spotted liquid sample). The term "spreading layer capable of metering a liquid sample" herein used refers to a layer having a function capable of spreading an applied liquid in such a manner that the spread area of the liquid is approximately in proportion to the amount of the liquid when the liquid is applied thereon and further having a function capable of supplying the liquid to the buffer layer. The porous spreading layer has voids allowing each migration or diffusion of the analyte (i.e., alkaline phosphatase).

The matrix of the spreading layer is chosen from the above-described materials according to the analytical conditions. When the sample containing insoluble materials which are inhibitors to the analysis (e.g., whole blood containing blood cell) is applied, the woven fabric and the knitted fabric which have a function to eliminate such inhibitors are most advantageous.

Examples of the woven fabrics (woven cloth) which can be used for the porous reagent layer include those disclosed in Japanese Patent Provisional Publications No. 55(1980)-164356 and No. 57(1982)-66359. Among the woven fabrics, plain weave fabrics made of warp and weft are preferred. Among plain woven fabrics, thin cloth, muslin, broadcloth and poplin are preferred.

Examples of yarns for woven cloth include those composed of the same materials as those constituting knitted cloths as described in more detail hereinafter. Any of filament yarn and spun yarn (twist yarn) can be used, and the spun yarn is preferred. The yarn diameter of the woven fabric is generally in the range of about 20 S to about 150 S, preferably about 40 S to about 120 S in terms of cotton spinning yarn count or in the range of about 35 to about 300 D, preferably about 45 to about 130 D in terms of silk thread denier. The thickness of the woven fabric is generally in the range of about 100 to about 500 $\mu$m, preferably about 120 to 350 $\mu$m. The voids of the woven fabroc are generally in the range of about 40 to about 90%, preferably about 50 to about 85%.

Examples of the knitted fabrics which can be used for the porous reagent layer include many kinds of knitted fabrics, among which warp knitted fabric and weft knitted fabric are preferred. Examples of the warp knitted fabrics include single atlas knitted cloth, tricot knitted cloth, double tricot knitted cloth, milanese knitted cloth and rashar knitted cloth. Examples of the weft knitted fabrics include plain weave knitted cloth, pearl knitted cloth, rib stitch cloth, and double face knitted cloth. Examples of the yarns for knitted fabrics include yarns of natural fibers such as cotton, silk and wool; yarns composed of fine fibers or single fibers of regenerated cellulose (e.g. viscose rayon and cupra), semi-synthetic organic polymer (e.g. cellulose diacetate and cellulose triacetate), synthetic organic polymer (e.g. polyamide such as nylon, acetalated polyvinyl alcohol such as vinylon, polyacrylonitrile, polyethylene terephthalate, polyethylene, polypropylene and polyurethane), and yarns composed of fiber blends of a natural fiber and a regenerated cellulose or a semi-synthetic or synthetic organic polymer fiber. Any of filament yarn and spun yarn can be used, and spun yarn is preferred. The diameter of the yarn for knitted fabric is generally in the range of from about 40 to 150 S, preferably about 60 to about 120 S in terms of cotton spinning yarn count, or in the range of about 35 to about 130 D, preferably about 45 to about 90 D in terms of silk thread denier. The number of knitting gauge of the knitted fabric is generally in the range of about 20 to about 50. The thickness of the knitted fabric is generally in the range of about 100 to about 600 μm, preferably about 150 to about 400 μm. The voids of the knitted fabric are generally in the range of about 40 to about 90%, preferably about 50 to about 85%. The warp knitted fabric, tricot knitted cloth, rashar knitted cloth, milanese knitted cloth and double tricot knitted cloth are preferred, because shrinkage in the wale's direction is small, the operation in the lamination stage of knitted goods is easy and the stitches are not easily loosened during cutting.

Woven fabric or knitted fabric is preferably a fabric from which fat is substantially removed when the yarn or the fabric is prepared. The fabrics are more preferably processed to be hydrophilic to enhance the adhesion to an underlying layer. Examples of such process to make the fabric hydrophilic include physical activating process (preferably glow discharge process or corona discharge process) disclosed in Japanese Patent Provisional Publication No. 57(1982)-66359 and hydrophilic polymer permeating process disclosed in Japanese Patent Provisional Publications Nos. 55(1980)-164356 and 57(1982)-66359.

The spreading layer constituted of woven fabric or knitted fabric can be laminated on the buffer layer or the adhesive layer according to the process disclosed in Japanese Patent Provisional Publications No. 55(1980)-164356 and No. 57(1982)-66359. The process is that woven fabric or knitted fabric is laminated under the substantially uniform light pressure on the wet or swelling buffer layer or adhesive layer which has been still wet condition after coating or has been supplied with water (or water containing small amount of detergent) after drying.

When the buffer layer or the adhesive layer is made of gelatin or gelatin derivatives, the spreading layer made of woven fabric or knitted fabric is preferably laminated on the wet or swelling gelatin (derivatives) of buffer layer or adhesive layer which has been still wet condition after coating.

In the integral multilayer analytical element of the invention for use in the measurement of ALP activity, the self-developing substrate is incorporated in the spreading layer. The term "self-developing substrate" used herein refers to a substance which undergoes a hydrolytic reaction as a substrate for alkaline phosphatase to generate a detectable color or to produce a detectable change in color. As the self-developing substrate, self-developing aryl phosphate amine salts are preferred from the viewpoint of preservation. The particularly preferred self-developing aryl phosphate amine salts are the monoor diamine salts of monoaryl phosphate esters which exhibit absorption spectrums in the visible ray region or 400 nm or above.

Examples of aryl phosphates which constitute the self-developing aryl phosphate amine salts include p-nitrophenyl phosphate, phenolphthalein monophosphate, thymolphthalein monophosphate and o-methylfluorescein phosphate described in the literature [Bower G. M.; Clin. Chem. Vol. 13, No. 7, 608–610 (1967)]. Further, there can be used arylazo-substituted aryl phosphates described in Japanese Patent Provisional Publication No. 57(1982)-15499.

Examples of the self-developing aryl phosphate amine salts include p-nitrophenyl phosphate bis(2-amino-2-methyl-1,3-propanediol) salt, p-nitrophenyl phosphate bis(cyclohexylamine) salt, p-nitrophenyl phosphate bis(-2-amino-2-ethyl-1,3-propanediol) salt, p-nitrophenyl phosphate bis(dicyclohexylamine) salt, p-nitrophenyl phosphate diTRIS salt (the term "TRIS" means tris(hydroxylmethyl)aminomethane), 4-nitronaphthyl phosphate bis(2-amino-2-ethyl-1,3-propanediol) salt, thymolphthalein monophosphate bis-(cyclohexylamine) salt, 4-phenylazonaphthyl phosphate bis(2-ethylaminoethanol) salt, phenolphthalein monophosphate bis(N-methylglucamine) salt, 4-nitrophenyl monophosphate bis-(2-amino-2-ethylpropanol) salt, 4-nitrophenyl monophosphate bis (2-ethylethanol) salt and 4-nitrophenyl monophosphate bis(2-(isopropylamino)ethanol) salt.

It is desirable that the self-developing substrate is incorporated in the spreading layer so as not to be brought into contact with the buffering agent in the buffer layer. For example, the incorporation of the self-developing substrate in the spreading layer is performed in such a manner that a laminated structure obtained by laminating the buffer layer and the spreading layer in turn onto a support as described above is coated or impregnated with a coating solution of the self-developing substrate and optionally a surfactant and a high molecular compound dissolved in an organic solvent or a mixture of an organic solvent and water.

Examples of such organic solvents include water-soluble polar solvents such as methanol, ethanol, propanol, acetone and acetonitrile; and hydrophobic solvents such as toluene and ethyl acetate.

When the spreading layer is composed of a material to be laminated by lamination, such as woven fabric or glass fiber filter paper, the substrate may be previously impregnated, dried and then laminated. When the spreading layer is formed by coating, for example, the spreading layer is composed of a brushed polymer layer or three-dimensional lattice-form structure using microbeads, the coating solutions for the substrate and the spreading layer may be mixed together and applied.

In addition to the self-developing substrate, a light blocking fine particle or reagents such as surfactant may be incorporated into the spreading layer of the analytical element of the invention. These reagents may be mixed with the coating solution for the substrate to incorporate it in the spreading layer, or the reagents and the substrate may be separately incorporated in the spreading layer by other methods.

The integral multilayer analytical element of the present invention for use in the measurement of ALP activity comprises a support, a buffer layer and a spreading layer in the form of a laminate and it is preferred that the buffer layer is laminated onto the support and the spreading layer is then laminated thereon. It will be understood that the integral multilayer analytical element of the invention may contain other functional layer or layers in addition to the essential layers described above.

The following examples and comparison example are provided to illustrate the present invention without limiting it thereto.

EXAMPLE 1

The surface of a transparent polyethylene terephthalate support of 180 μm thick was treated to make it hydrophilic. The treated surface was coated with a coating solution of the following composition and dried to form a buffer layer of 15 μm in dry film thickness.

| Coating solution for buffer layer formation: | |
| --- | --- |
| Alkali-treated deionized gelatin | 10 g |
| Octylphenoxy polyethoxyethanol | 0.5 g |
| Water | 100 ml |
| 2-Amino-2-methyl-1-propanol | 1 M solution |

A coating solution of the following composition was then coated on the surface of the formed buffer layer and dried to form a bonding layer of 3 μm in dry film thickness.

| Coating solution for bonding layer formation: | |
| --- | --- |
| Gelatin | 36 g |
| Water | 560 g |
| Nonylphenoxy polyglycidol | 2 g |

A polyester twisted yarn tricot knitted fabric spreading layer of 250 μm thick was bonded to the surface of the bonding layer by means of a wet-process laminating method.

The spreading layer was coated with a 50% aqueous ethanol solution of 50 mM p-nitrophenyl phosphate diTRIS salt in such an amount as to give a coating weight of 6 m mol/m$^2$ (in terms of said salt) and dried.

In this way, there was prepared an integral multilayer analytical element for use in the measurement of ALP activity according to the present invention.

EXAMPLE 2

The procedure of Example 1 was repeated except that an aqueous solution of 50 mM disodium p-nitrophenyl phosphate was used in place of p-nitrophenyl phosphate diTRIS salt to prepare an integral multilayer analytical element according to the present invention.

COMPARISON EXAMPLE 1

A buffer layer was formed on the surface of the support in the same manner as in Example 1 except that 2-amino-2-methyl-1-propanol was omitted. A polyester tricot spreading layer was then bonded to the buffer layer.

In a similar manner to that described in Example 1, the spreading layer was coated with 1M 2-amino-2-methyl-1-propanol and an aqueous solution of 50 mM disodium p-nitrophenyl phosphate and dried to prepare an integral multilayer analytical element for use in the measurement of ALP activity.

Fog reflection density (after drying) of each of the analytical elements prepared in the above Examples and Comparison Example was measured from the support side of the element and the stability of the substrates was compared. The results are set forth in Table 1. The fog reflection density is optical reflection density obtained by conducting reflection photometry from the support side of an unused analytical element.

TABLE 1

| Analytical element | Fog optical reflection density (OD) |
| --- | --- |
| Example 1 | 0.593 |
| Example 2 | 0.716 |
| Comparison Example 1 | 0.958 |

EXAMPLE 3

The procedure of Example 1 was repeated except that p-nitrophenyl phosphate bis(cyclohexyl)amine salt was used in place of p-nitrophenyl phosphate diTRIS salt to prepare an integral multilayer analytical element for use in the measurement of ALP activity.

EXAMPLE 4

The procedure of Example 1 was repeated except that 2-(isopropylamino)ethanol (pKa 9.7) was used in place of 2-amino-2-methyl-1-propanol to prepare an integral multilayer analytical element for use in the measurement of ALP activity.

EXAMPLE 5

The procedure of Example 1 was repeated except that diethanolamine (pKa 8.7) was used in place of 2-amino-2-methyl-1-propanol to prepare an integral multilayer analytical element for use in the measurement of ALP activity.

Fog optical reflection density of each of the analytical elements prepared in Examples 3 to 5 immediately after being dried as well as after storage for 7 days at 45° C. was measured from the support side of the element and the stability of the substrate contained in the analytical element was examined. The results are set forth in Table 2.

TABLE 2

| Analytical element | Fog optical reflection density (OD) | |
| --- | --- | --- |
| | immediately after drying | after 7 days |
| Example 3 | 0.557 | 1.110 |
| Example 4 | 0.545 | 1.045 |
| Example 5 | 0.704 | 1.560 |

EXAMPLE 6

The surface of a transparent support of polyethylene terephthalate of 180 μm thick was treated to make it hydrophilic. The treated surface was coated with a coating solution of the following composition in such an amount as to give a dry film of 10 μm in thickness, thus forming a buffer layer.

| Coating solution for buffer layer formation: | |
| --- | --- |
| Gelatin | 33 g |
| Water | 225 g |
| Nonylphenoxy polyglycidol | 1.1 g |
| 2-(Ethylamino)ethanol | 26.7 g |
| N—(2-hydroxyethyl)ethylenediamine-N,N',N'-triacetic acid | 2 mmol |
| Zn(C$_2$H$_3$OO)$_2$.2H$_2$O | 1 mmol |
| MgSO$_4$.7H$_2$O | 2 mmol |

The pH of the above solution was adjusted to 10.5 by the addition of 6N Hcl.

A coating solution of the following composition was applied to the surface of the above buffer layer in such an amount as to give a film of 3.6 μm in dry thickness to form a bonding layer.

| Coating solution for bonding layer formation: | |
|---|---|
| Gelatin | 36 g |
| Water | 560 g |
| Nonylphenoxy polyglycidol | 2 g |

The surface of the above bonding layer was coated with aqueous 0.4% nonylphenoxy polycidol solution. Tricot knitted fabric composed of 36 gauge 50 D polyethylene terephthalate spun yarn was laminated thereon and the laminate was compressed under pressure to form a spreading layer.

The spreading layer was coated with a coating solution of the following composition in such an amount as to give 60 ml/m², and dried.

| Coating solution containing self-developing substrate: | |
|---|---|
| p-Nitrophenyl phosphate bis-2-amino-2-ethyl-1,3-propanediol) salt | 30 mmol |
| Water | 10 g |
| Polyvinyl pyrrolidone (average molecular weight: 100,000) | 6 g |
| Ethanol | 22 g |

Further, a coating solution of the following composition was coated thereon in such an amount as to give 60 ml/m² and dried.

| Coating solution for light-blocking fine particle: | |
|---|---|
| Fine TiO₂ particle | 5 g |
| 1% Aqueous solution of hydroxypropylmethylcellulose (2% aqueous solution having a viscosity of 40 to 60 cPs at 20° C.) | 100 g |
| Nonylphenoxy polyglycidol | 0.6 g |

The analytical characteristics of the integral multilayer analytical element of the present invention for use in the measurement of ALP activity, which were prepared by the above-described method, were evaluated.

The above analytical element was cut into a square (15 mm square) and put in a plastic mount (described in Japanese Patent Provisional Publication No. 57(1982)-63452) to prepare a slide for the analysis of ALP.

Each of 10 μl of human serums having an ALP activity of 50, 96, 481, 906 and 1250 IU/l at 37° C. (said ALP activity being assayed by IFCC method which is a standard analytical method for the measurement of ALP activity) was spotted on the spreading layer of the analytical element of each mount, and each slide was left to stand on a 37° C. constant temperature heating plate in which the deposition of moisture was completely controlled. The measurement of optical reflection density was made at the central wavelength of 410 nm after 2 min. and 5 min. The results are set forth in Table 3.

TABLE 3

| ALP activity (IU/l) | OD (5 min–2 min) |
|---|---|
| 50 | 0.0030 |
| 96 | 0.0120 |
| 481 | 0.0625 |
| 906 | 0.1160 |

TABLE 3-continued

| ALP activity (IU/l) | OD (5 min–2 min) |
|---|---|
| 1250 | 0.1485 |

It has been confirmed from the above results that the correlation between ALP activity and an increase in optical density is positive and hence, the slide is effectively employable as the analytical element for the measurement of ALP activity.

EXAMPLE 7

The procedure of Example 6 was repeated except that an equal equivalent amount of each of 2-(methylamino)ethanol, 2-(isopropylamino)ethanol and DL-2-amino-2-methyl-1-propanol was used in place of 2-(ethylamino)ethanol to prepare an integral multilayer analytical element for the measurement of ALP activity.

Analytical slides were prepared from each of the above analytical elements in a similar manner to that described in Example 6, and the analytical characteristics thereof were evaluated. Each slide gave a calibration curve in proportion to the ALP activity of each analyte.

A test on the preservation of the substrate for each slide was conducted in a similar manner to that described in Examples 1 to 5 and all slides exhibited satisfactory preservation.

EXAMPLE 8

The procedure of Example 4 was repeated except that 3 g of 2-(dimethylamino)ethanol was used in place of 26.7 g of 2-(ethylamino)ethanol in the coating solution for buffer layer formation in Example 6 and further 1.6 g of sodium carbonate and 0.3 g of bis(vinylsulfonylmethyl)ether was added to form a buffer layer.

The surface of the spreading layer was coated with a coating solution of the following composition in an amount of 60 ml/m² and dried to prepare an integral multilayer analytical element for the measurement of ALP activity.

| Coating solution containing self-developing substrate | |
|---|---|
| p-Nitrophenyl phosphate bis (2-amino-2-ethyl-1,3-propanediol salt | 30 mmol |
| Water | 10 g |
| Polyvinyl pyrrolidon (average molecular weight: 100,000) | 6 g |
| Ethanol | 30 g |
| Fine TiO₂ particle | 5 g |

The resulting analytical element was tested to examine the correlation between the ALP activity and the optical reflection density in a similar manner to that described in Example 6, and similar results to those of Example 6 were obtained.

The fog optical reflection density of the analytical element immediately after being dried and after storage for 7 days at 45° C. was measured from the support side of the element. The results are set forth in Table 4.

TABLE 4

| Analytical element | Fog optical reflection density (OD) | |
|---|---|---|
| | immediately after drying | after 7 days |
| Example 8 | 0.345 | 0.453 |

We claim:

1. An integral multilayer analytical element for use in the measurement of alkaline phosphatase activity, which comprises in sequential order a porous spreading layer of woven fabric or knitted fabric containing an alkaline phosphatase-sensitive self-developing substrate, a buffer layer containing a compound functioning as a phosphoric acid acceptor and a buffering agent and a support layer in a laminated form.

2. The integral multilayer analytical element as claimed in claim 1, wherein said phosphoric acid acceptor is an amino-alcohol having a pKa value of not lower than 9.0.

3. The integral multilayer analytical element as claimed in claim 2, wherein said amino-alcohol is a member selected from the group consisting of 2-(methylamino)ethanol, 2-(dimethylamino)ethanol, 2-(isopropylamino)ethanol, 2-(ethylamino)ethanol, 3-aminopropanol, DL-2-amino-1-propanol, N-methylglucamine, hydroxyproline, 2-aminoethanol and 2-amino-2-methyl-1-propanol.

4. The integral multilayer analytical element as claimed in claim 1, wherein said self-developing substrate is a self-developing aryl phosphate amine salt.

5. The integral multilayer analytical element as claimed in claim 4, wherein said self-developing aryl phosphate amine salt contains an aryl group selected from the group consisting of nitro-substituted phenyl, phenolphthalein, thymolphthalein, arylazo-substituted aryl group and fluorescein group and the amine of said salt is selected from the group consisting of tris(hydroxymethyl)aminomethane, 2-amino-2-methyl-1,3-propanediol, 2-amino-2-ethyl-1,3-propanediol, bis(cyclohexyl)amine, 2-(ethylamino)ethanol, N-methylglucamine, 2-(methylamino)ethanol, 2-(dimethylamino)ethanol, 2-(isopropylamino)ethanol and 2-amino-2-methyl-1-propanol.

6. The integral multilayer analytical element as claimed in claim 4 wherein said phosphoric acid acceptor is an amino-alcohol having a pKa value of not lower than 9.0.

7. The integral multilayer analytical element as claimed in claim 6 wherein said amino-alcohol is a member selected from the group consisting of 2-(methylamino)ethanol, 2-(dimethylamino)ethanol, 2-(isopropylamino)ethanol, 2-(ethylamino)ethanol, 3-aminopropanol, DL-2-amino-1-propanol, N-methylglucamine, hydroxyproline, 2-aminoethanol and 2-amino-2-methyl-1-propanol.

* * * * *